(12) United States Patent
Lobell et al.

(10) Patent No.: US 11,884,660 B2
(45) Date of Patent: Jan. 30, 2024

(54) SUBSTITUTED OXOPYRIDINE DERIVATIVE

(71) Applicant: Bayer Pharma Aktiengesellschaft, Berlin (DE)

(72) Inventors: Mario Lobell, Wuppertal (DE); Hartmut Schirok, Langenfeld (DE); Adrian Tersteegen, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 762 days.

(21) Appl. No.: 17/046,004

(22) PCT Filed: Apr. 3, 2019

(86) PCT No.: PCT/EP2019/058398
§ 371 (c)(1),
(2) Date: Oct. 8, 2020

(87) PCT Pub. No.: WO2019/197244
PCT Pub. Date: Oct. 17, 2019

(65) Prior Publication Data
US 2021/0147414 A1    May 20, 2021

(30) Foreign Application Priority Data
Apr. 10, 2018   (EP) ..................... 18166490

(51) Int. Cl.
*C07D 471/04*    (2006.01)
*A61K 47/36*    (2006.01)
*A61P 7/02*    (2006.01)
*A01N 1/00*    (2006.01)
*A61K 9/00*    (2006.01)
*A61K 9/20*    (2006.01)

(52) U.S. Cl.
CPC ............ *C07D 471/04* (2013.01); *A01N 1/00* (2013.01); *A61K 9/0048* (2013.01); *A61K 9/2013* (2013.01); *A61K 9/2018* (2013.01); *A61K 9/2027* (2013.01); *A61K 9/2059* (2013.01); *A61K 47/36* (2013.01); *A61P 7/02* (2018.01)

(58) Field of Classification Search
CPC ................................... C07D 471/04
See application file for complete search history.

(56) References Cited

U.S. PATENT DOCUMENTS

| | | |
|---|---|---|
| 9,434,690 B2 | 9/2016 | Roehrig et al. |
| 9,475,809 B2 | 10/2016 | Roehrig et al. |
| 9,765,070 B2 | 9/2017 | Roehrig et al. |
| 9,822,102 B2 | 11/2017 | Roehrig et al. |
| 9,918,969 B2 | 3/2018 | Roehrig et al. |
| 10,071,995 B2 | 9/2018 | Roehrig et al. |
| 10,077,265 B2 | 9/2018 | Roehrig et al. |
| 10,138,236 B2 | 11/2018 | Roehrig et al. |
| 10,167,280 B2 | 1/2019 | Roehrig et al. |
| 10,183,932 B2 | 1/2019 | Roehrig et al. |
| 10,414,731 B2 | 9/2019 | Roehrig et al. |
| 10,421,742 B2 | 9/2019 | Jimenez Nunez et al. |
| 2017/0298052 A1 | 10/2017 | Roehrig et al. |
| 2018/0250280 A1 | 9/2018 | Jimenez Nunez et al. |
| 2019/0119213 A1 | 4/2019 | Roehrig et al. |
| 2019/0367478 A1 | 12/2019 | Jimenez Nunez et al. |

FOREIGN PATENT DOCUMENTS

| | | | |
|---|---|---|---|
| EP | WO 2015-063093 | * | 5/2015 |
| WO | 2005/123680 A1 | | 12/2005 |
| WO | 2006/030032 A1 | | 3/2006 |
| WO | 2008/079787 A2 | | 7/2008 |
| WO | 2014/154794 A1 | | 10/2014 |

(Continued)

OTHER PUBLICATIONS

PCT International Search Report for PCT/EP2019/058398, dated May 8, 2019.

*Primary Examiner* — Valerie Rodriguez-Garcia
(74) *Attorney, Agent, or Firm* — McBee Moore & Vanik, IP, LLC

(57) ABSTRACT

The invention relates to 5-({6-amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide (I)

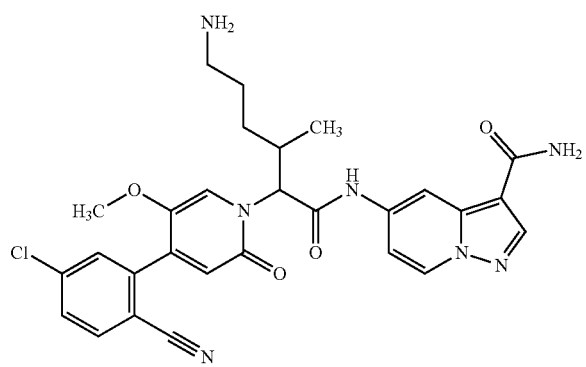

to processes for its preparation, to its use for the treatment and/or prophylaxis of diseases and to its use for the preparation of medicaments for the treatment and/or prophylaxis of diseases, in particular cardiovascular disorders, preferably thrombotic or thromboembolic disorders, and edemas, and also ophthalmic disorders, and its use to inhibit disturbing plasma kallikrein activity for the conduct of extracorporeal procedures and analytical assays.

7 Claims, No Drawings

(56) References Cited

FOREIGN PATENT DOCUMENTS

| | | |
|---|---|---|
| WO | 2014/160592 A2 | 10/2014 |
| WO | 2015/011087 A1 | 1/2015 |
| WO | 2015/063093 A1 | 5/2015 |
| WO | 2015/120777 A1 | 8/2015 |
| WO | 2016/046156 A1 | 3/2016 |
| WO | 2016/046157 A1 | 3/2016 |
| WO | 2016/046158 A1 | 3/2016 |
| WO | 2016/046159 A1 | 3/2016 |
| WO | 2016/046164 A1 | 3/2016 |
| WO | 2016/046166 A1 | 3/2016 |
| WO | 2016/146606 A1 | 9/2016 |
| WO | 2017/005725 A1 | 1/2017 |
| WO | 2017/037051 A1 | 3/2017 |
| WO | 2018/041122 A1 | 3/2018 |

* cited by examiner

SUBSTITUTED OXOPYRIDINE DERIVATIVE

CROSS-REFERENCE TO RELATED APPLICATIONS

This application is the National Stage entry of International Application No. PCT/EP2019/058398, filed 3 Apr. 2019, which claims priority to European Patent Application No. 18166490.5, filed 10 Apr. 2018.

BACKGROUND

Field

The invention relates to 5-({6-amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide, to processes for its preparation, to its use for the treatment and/or prophylaxis of diseases and to its use for the preparation of medicaments for the treatment and/or prophylaxis of diseases, in particular cardiovascular disorders, preferably thrombotic or thromboembolic disorders, and edemas, and also ophthalmic disorders, and its use to inhibit disturbing plasma kallikrein activity for the conduct of extracorporeal procedures and analytical assays.

Description of Related Art

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot.

It becomes the focus that the coagulation system can be activated particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa which subsequently activates factor XI to factor XIa. In addition, factor XIIa also activates plasma prekallikrein (PPK) to plasma kallikrein (PK) which, in a potentiation loop, firstly leads to further factor XII activation, overall resulting in amplification of the initiation of the coagulation cascade. In addition, PK is an important bradikinin-releasing protease which, inter alia, thus leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Uncontrolled activation of the coagulation system or defective inhibition of the activation processes may lead to the formation of local thromboses or embolisms in vessels (arteries, veins, lymph vessels) or cardiac cavities. In addition, systemic hypercoagulability may lead to system-wide formation of thrombi and finally to consumption coagulopathy in the context of a disseminated intravasal coagulation. Thromboembolic complications may also occur in extracorporeal circulatory systems such as during haemodialysis and also in vascular prostheses or prosthetic heart valves and stents.

Plasma kallikrein (PK) is associated with other disorders, which are associated with increased vascular permeability or chronic inflammatory disorders such as is the case in diabetic retinopathy, macular edema and hereditary angioedema or chronic inflammatory intestinal disorders. Diabetic retinopathy is primarily caused by microvascular deficiency, which leads to basal membrane thickening of the vessels and loss of vascularized pericytes followed by vascular occlusion and retinal ischaemia which, owing to the retinal hypoxia thus caused, may lead to enhanced vessel permeability with subsequent formation of a macular edema and, due to all of the processes present, to the patient going blind. In hereditary angioedema (HAE), reduced formation of the physiological kallikrein inhibitor Cl-esterase inhibitor causes uncontrolled plasma kallikrein activation leading to inflammations with fulminant edema formation and strong pains. From experimental animal models, there are indications that inhibition of plasma kallikrein inhibits increased vascular permeability and may therefore prevent formation of a macular edema and/or diabetic retinopathy or may improve the acute symptoms of HAE. Oral plasma kallikrein inhibitors could also be used for prophylaxis of HAE.

The kinins generated by means of plasma kallikrein especially have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

For many disorders the combination of antithrombotic and antiinflammatory principles may also be particularly attractive to prevent the mutual enhancement of coagulation and inflammation. WO 2006/030032 describes inter alia substituted pyridinones as allosteric modulators of the mGluR2 receptor, and WO 2008/079787 describes substituted pyridin-2-ones and their use as glucokinase activators. WO2005/123680, WO 2014/154794, WO 2014/160592, WO 2015/011087, WO 2015/063093, WO 2015/120777, WO 2016/046156, WO 2016/046157, WO 2016/046158, WO 2016/046159, WO 2016/046164, WO 2016/046166, WO 2016/146606, WO 2017/005725, WO 2017/037051 and WO 2018/041122 describe substituted pyridin-2-one and their use as factor XIa inhibitors and/or kallikrein inhibitors.

SUMMARY

It is therefore an object of the present invention to provide a novel compound for the treatment of cardiovascular disorders, in particular of thrombotic or thromboembolic disorders, in humans and animals, and for the use in plasma prekallikrein (PPK) or plasma kallikrein (PK) containing biological samples to prevent disturbing effects caused by the turnover of physiological and artificial substrates by PK.

Surprisingly, it has now been found that a certain substituted oxopyridine derivative represents a highly potent and selective plasma kallikrein inhibitor.

The invention provides the compound 5-({6-amino-2-[4-(5-chloro-2-cyanophenyl)-5-methoxy-2-oxopyridin-1(2H)- yl]-3-methylhexanoyl}amino)pyrazolo[1,5-a]pyridine-3-carboxamide, which corresponds to the compound of the formula (I)

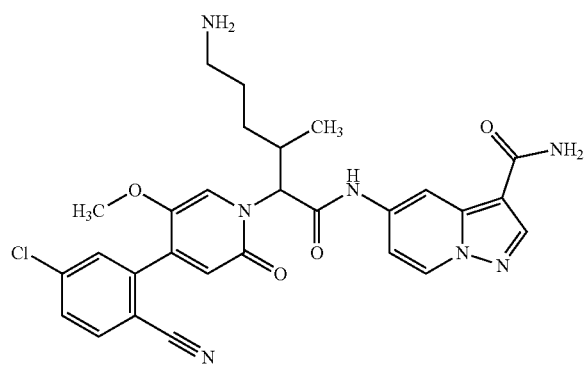

(I)

and the salts thereof, the solvates thereof and the solvates of the salts thereof.

DETAILED DESCRIPTION OF A PREFERRED EMBODIMENT

Furthermore, the invention provides the compound 5-({6-amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide trifluoroacetate, which corresponds to the compound of the formula (Ia)

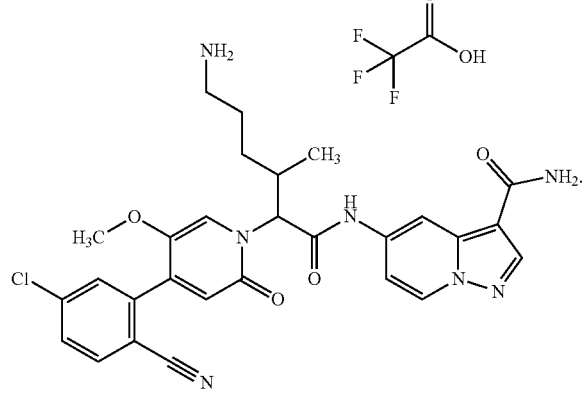

(Ia)

Preference is given to the compound 5-({(2S)-6-amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide, which corresponds to the compound of the formula (Ib)

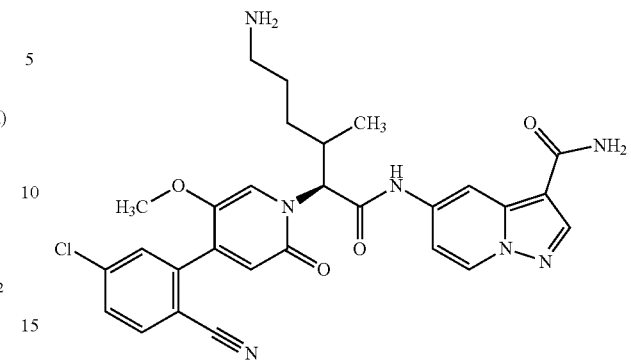

(Ib)

and the salts thereof, the solvates thereof and the solvates of the salts thereof.

Furthermore, preference is given to the compound 5-({(2S)-6-amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide trifluoroacetate, which corresponds to the compound of the formula (Ic)

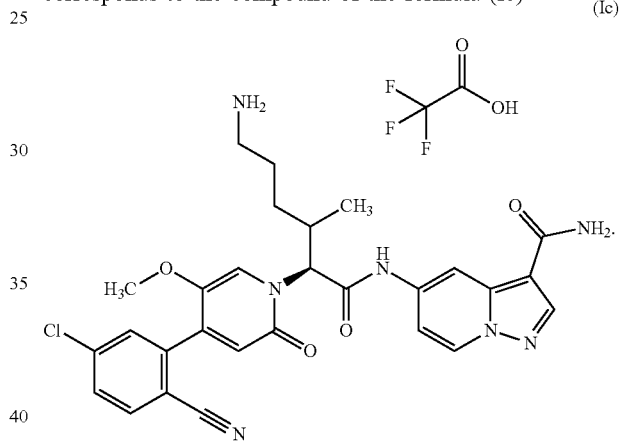

(Ic)

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

In the context of the present invention, the term "enantiomerically pure" is to be understood as meaning that the compound in question with respect to the absolute configuration of the chiral centre is present in an enantiomeric excess of more than 95%, preferably more than 97%. The enantiomeric excess, ee, is calculated here by evaluating the corresponding HPLC chromatogram on a chiral phase using the formula below:

$$ee = [E^A \text{ (area \%)} - E^B \text{ (area \%)}] \times 100\% / [E^A \text{ (area \%)} + E^B \text{ (area \%)}]$$

($E^A$: major enantiomer, $E^B$: minor enantiomer)

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^{2}$H (deuterium), $^{3}$H (tritium), $^{13}$C, $^{14}$C, $^{15}$N, $^{17}$O, $^{18}$O and $^{36}$Cl. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^{3}$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Designated as solvates in the context of the invention are those forms of the compounds according to the invention which form a complex in the solid or liquid state by coordination with solvent molecules. Hydrates are a specific form of the solvates in which the coordination is with water.

The present invention additionally also encompasses prodrugs of the compounds of the invention. The term "prodrugs" encompasses compounds which for their part may be biologically active or inactive but are converted during their residence time in the body into compounds according to the invention (for example by metabolism or hydrolysis).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is used here synonymously with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The invention further provides a process for preparing the compounds of the formula (I), (Ia), (Ib) and (Ic), or the salts thereof, solvates thereof or the solvates of the salts thereof. The compounds can be synthesised as illustrated in synthetic scheme 1:

Scheme 1

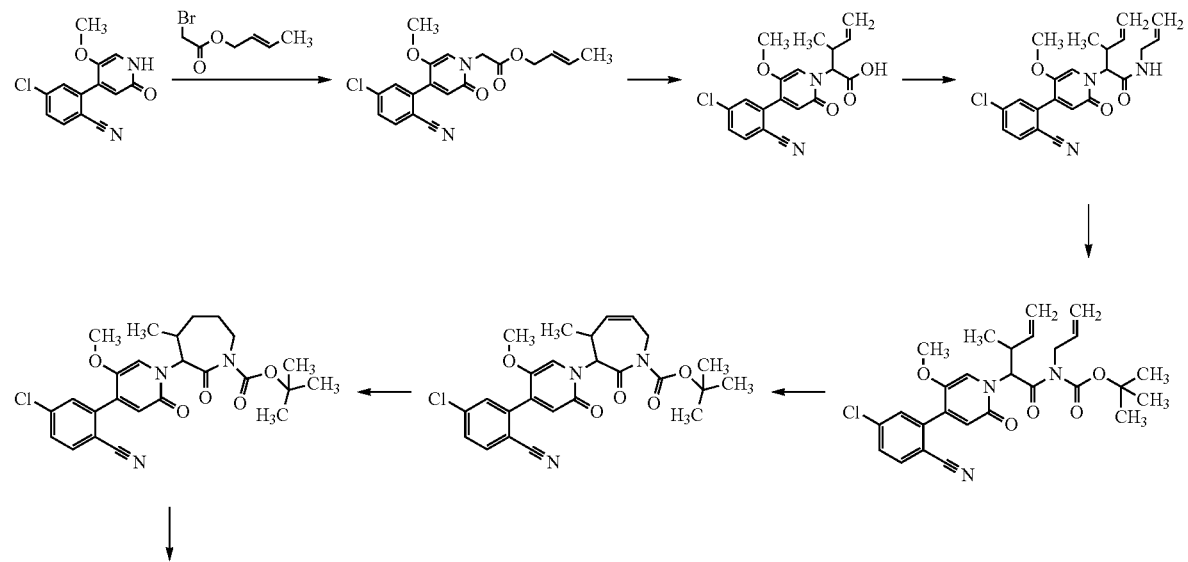

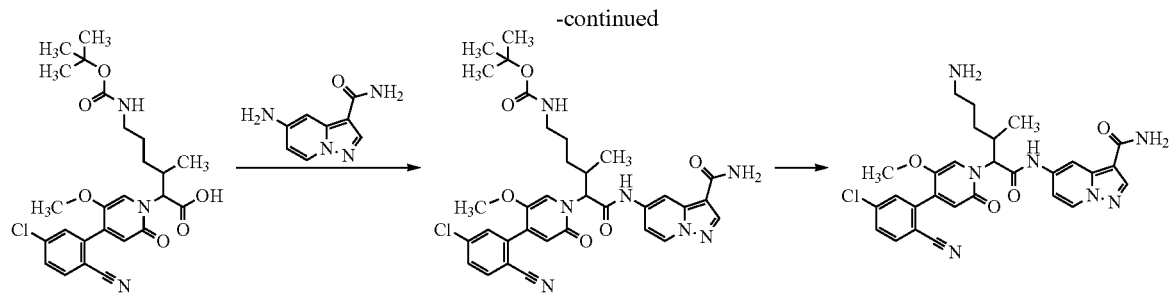
-continued

The compounds according to the invention have an unforeseeable useful pharmacological activity spectrum. They are compounds that influence the proteolytic activity of the serine protease plasma kallikrein (PK). The compounds according to the invention inhibit the enzymatic cleavage of substrates, catalysed by PK, which have essential roles in the activation of blood coagulation, in the aggregation of blood platelets, and in inflammatory processes, which particularly involve an increase in vascular permeability.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmic disorders, in particular of diabetic retinopathy or macular edema, and/or inflammatory disorders, in particular those associated with excess plasma kallikrein activity, such as hereditary angioedema (HAE) or chronic inflammatory disorders, particularly of the intestine such as Crohn's disease.

Factor XIIa activates plasma prekallikrein (PPK) to plasma kallikrein (PK) in the context of the intrinsic activation which, inter alia, in a potentiation loop, leads to further factor XII activation, overall resulting in amplification of the initiation of the coagulation cascade on surfaces. A PK-inhibiting activity of a compound according to the invention thus reduces coagulation via surface activation and thus has an anticoagulatory effect.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

The inventive compounds are therefore also suitable for the prevention and treatment of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves.

In addition, the inventive compounds are suitable for the treatment and prevention of disseminated intravascular coagulation (DIC) which may occur in connection with sepsis inter alia, but also owing to surgical interventions, neoplastic disorders, burns or other injuries and may lead to severe organ damage through microthromboses.

Thromboembolic complications furthermore occur in microangiopathic haemolytical anaemias and by the blood coming into contact with foreign surfaces in the context of extracorporeal circulation such as, for example, haemodialysis, ECMO ("extracorporeal membrane oxygenation"), LVAD ("left ventricular assist device") and similar methods, AV fistulas, vascular and heart valve prostheses.

Moreover, the compounds according to the invention are suitable for the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component also plays an essential role. Mutual enhancement of coagulation and inflammation in particular can be prevented by the compounds according to the invention, thus decisively lowering the probability of thrombotic complications. In this case, both the factor XIa-inhibitory component (via inhibition of thrombin production) and the PK-inhibitory component can contribute to the anticoagulant and antiinflammatory effect (e.g. via bradykinin). Therefore, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Kinins generated by means of plasma kallikrein, inter alia, have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Moreover, the compounds according to the invention can be used for inhibiting tumour growth and the formation of metastases, and also for the prophylaxis and/or treatment of thromboembolic complications, such as, for example, venous thromboembolisms, for tumour patients, in particular those undergoing major surgical interventions or chemo- or radiotherapy.

In addition, the compounds according to the invention are also suitable for the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and diffusion of fluid and proteins into the extravasal space. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or crosslinked extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

In addition to the anticoagulant activity, plasma kallikrein is an important bradykinin-releasing protease which, inter alia, thus leads to increased endothelial permeability. The compounds can therefore be used for the treatment and/or prophylaxis of disorders involving edema formations such as ophthalmic disorders, in particular, diabetic retinopathy or macular edema or hereditary angioedema.

"Ophthalmic disorders" in the context of the present invention include in particular disorders such as diabetic retinopathy, diabetic macular edema (DME), macular edema, macular edema associated with retinal vein occlusion, age-related macular degeneration (AMD), choroidal neovascularization (CNV), choroidal neovascular membranes (CNVM), cystoid macular edema (CME), epiretinal membranes (ERM) and macular perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorders such as uveitis, scleritis or endophthalmitis, cataract, refraction anomalies such as myopia, hyperopia or astigmatism and keratoconus, disorders of the anterior eye such as corneal angiogenesis as sequela of, for example, keratitis, cornea transplantation or keratoplasty, corneal angiogenesis as sequela of hypoxia (for example by excessive use of contact lenses), pterygium conjunctivae, subcorneal edema and intracorneal edema.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

Particular the present invention provides the compounds according to the invention for use in a method for the treatment and/or prophylaxis of thrombotic or thromboembolic disorders using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo.

The compounds according to the invention can also be used in plasma prekallikrein (PPK) or plasma kallikrein (PK) containing biological samples to prevent disturbing effects caused by the turnover of physiological and artificial substrates by PK.

The present invention furthermore provides a method for preventing the coagulation of blood in vitro, in particular in banked blood or biological samples which may comprise plasma kallikrein, which method is characterized in that an anticoagulatory effective amount of the compound according to the invention is added.

The present invention further provides medicaments comprising a compound according to the invention and one or more further active compounds, in particular for the treatment and/or prophylaxis of the disorders mentioned above.

"Combinations" for the purpose of the invention mean not only dosage forms which contain all the components (so-called fixed combinations) and combination packs which contain the components separate from one another, but also components which are administered simultaneously or sequentially, provided that they are used for the prophylaxis and/or treatment of the same disease. It is likewise possible to combine two or more active ingredients with one another, meaning that they are thus each in two-component or multicomponent combinations.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Suitable for extraocular (topic) administration are administration forms which operate in accordance with the prior art, which release the active compound rapidly and/or in a modified or controlled manner and which contain the active compound in crystalline and/or amorphized and/or dissolved form such as, for example, eye drops, sprays and lotions (e.g. solutions, suspensions, vesicular/colloidal systems, emulsions, aerosols), powders for eye drops, sprays and lotions (e.g. ground active compound, mixtures, lyophilisates, precipitated active compound), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable for intraocular administration are administration forms which operate in accordance with the prior art, which release the active compound rapidly and/or in a modified or controlled manner and which contain the active compound in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active compound, mixtures, lyophilisates, precipitated active compound), gels for preparations for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds of the invention can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments comprising at least one inventive compound, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary, if appropriate, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

A) EXAMPLES

Abbreviations aq. aqueous
Boc tert-butyloxycarbonyl br broad (in NMR)
brsm based on recovered starting material
d day(s), doublet (in NMR)
dd doublet of doublet (in NMR)
ddd doublet of doublet of doublet (in NMR)
DMF N,N-dimethylformamide
DMSO dimethyl sulphoxide
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
HV high vacuum
LC-MS liquid chromatography-coupled mass spectroscopy
m multiplet (in NMR)
min minute(s)
MS mass spectroscopy
NMR nuclear magnetic resonance spectroscopy
R$_t$ retention time (in HPLC)
s singlet (in NMR)
t triplet (in NMR)
THF tetrahydrofuran
TFA trifluoroacetic acid
T3P 2,4,6-tripropyl-1,3,5,2,4,6-trioxatriphosphinane 2,4,6-trioxide
LC-MS Methods:
Method 1: Instrument MS: Thermo Scientific FT-MS; HPLC instrument: Thermo Scientific UltiMate 3000; Column: Waters Acquity UPLC HSS T3, 100 Å, 1.8 µm, 2.1 mm×75 mm; Eluent A: 1 l water+0.01% formic acid; Eluent B: 1 l acetonitrile+0.01% formic acid; Gradient: 0.0 min 10% B→2.5 min 95% B→3.5 min 95% B; Oven: 50° C.; Flow: 0.90 ml/min; UV-detection: 210 nm/Optimum Integration Path 210-300 nm.
Method 2: Instrument: Waters ACQUITY SQD UPLC System; Column: Waters Acquity UPLC HSS T3, 100 Å, 1.8 µm; 1 mm×50 mm; Eluent A: 1 l water+0.25 ml 99% formic acid, Eluent B: 1 l acetonitrile+0.25 ml 99% formic acid; Gradient: 0.0 min 90% A→1.2 min 5% A→2.0 min 5% A; Oven: 50° C.; Flow: 0.40 ml/min; UV-Detection: 210 nm.

When compounds according to the invention are purified by chromatography in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Compounds

Example 1A (2E)-But-2-en-1-yl [4-(5-chloro-2-cyanophenyl)-5-methoxy-2-oxopyridin-1(2H)-yl]acetate

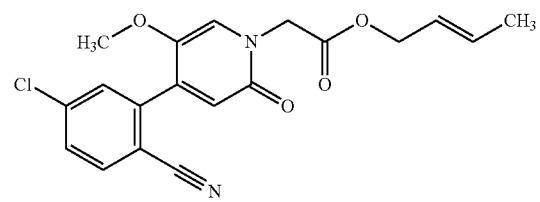 [SMILES: C/C=C/COC(=O)Cn1cc(OC)c(-c2cc(Cl)ccc2C#N)cc1=O]

A mixture of 4-chloro-2-(5-methoxy-2-oxo-1,2-dihydropyridin-4-yl)benzonitrile [CAS-RN 1630193-83-7; WO2015/063093, p. 73f., expl. 2.1 C] (11.3 g, 43.2 mmol), (2E)-but-2-en-1-yl bromoacetate [CAS-RN 93455-19-7; S. M. Weinreb et al., *J. Org. Chem.* 1984, 49, 5058-5064] (10.0 g, 51.8 mmol) and potassium carbonate (8.95 g, 64.8 mmol) in DMF (90 ml) was heated to 100° C. for 45 min. Subsequently, the solvent was removed in vacuo. Water was added and the mixture was extracted three times with ethyl acetate. The combined organic layers were washed with brine and dried over sodium sulfate. The solvent was evaporated and the residue purified by column chromatography (silica gel; eluent: cyclohexane-ethyl acetate gradient) to yield 10.8 g (92% purity, 62% yield) of the title compound.

LC-MS (Method 2): R$_t$=0.92 min; MS (ESIpos): m/z=373 [M+H]$^+$ $^1$H-NMR (400 MHz, DMSO-d$_6$): δ [ppm]=8.01-7.97 (m, 1H), 7.75-7.71 (m, 2H), 7.58 (s, 1H), 6.52 (s, 1H), 5.88-5.78 (m, 1H), 5.65-5.55 (m, 1H), 4.74 (s, 2H), 4.59 (d, 2H), 3.62 (s, 3H), 1.70 (dd, 3H).

Example 2A

2-[4-(5-Chloro-2-cyanophenyl)-5-methoxy-2-oxopyridin-1(2H)-yl]-3-methylpent-4-enoic acid (Racemic Mixture of Diastereomers)

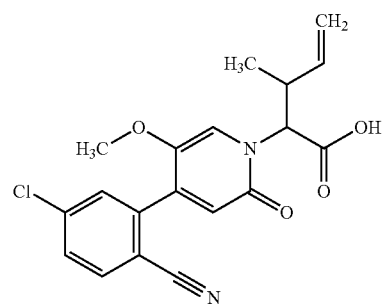 [SMILES: C=CC(C)C(C(=O)O)n1cc(OC)c(-c2cc(Cl)ccc2C#N)cc1=O]

(2E)-But-2-en-1-yl [4-(5-chloro-2-cyanophenyl)-5-methoxy-2-oxopyridin-1(2H)-yl]acetate (10.8 g, 92% purity, 26.7 mmol) was dissolved in THF (150 ml) and cooled to −78° C. Lithium bis(trimethylsilyl)amide (58 ml, 1.0 M in THF, 58 mmol) was added. The reaction was stirred for 30 min at −78° C. Subsequently, chloro(trimethyl)silane (7.4 ml, 58 mmol) was added. It was warmed to 60° C. and stirred for 1 h. Water was added to the reaction mixture and it was acidified with 1N aq. hydrochloric acid. It was extracted three times with dichloromethane. The combined organic layers were extracted three times with 1N aq. sodium hydroxide solution. The combined basic layers were acidified with 4N aq. hydrochloric acid and extracted five times with dichloromethane. The combined organic phases were dried over sodium sulfate and the solvent was evaporated to yield 6.95 g (70% yield) of the title compound as a racemic mixture of diastereomers (ratio 38:62).

LC-MS (Method 1): $R_t$=1.59 min (minor isomer), 1.62 min (major isomer); MS (ESIpos): m/z=373 $[M+H]^+$ $^1$H-NMR (400 MHz, DMSO-$d_6$): δ [ppm]=13.16 (br s, 1H), 7.99 (d, 1H major isomer) and 7.98 (d, 1H minor isomer), 7.76-7.69 (m, 2H), 7.44 (s, 1H major) and 7.38 (s, 1H minor), 6.52 (s, 1H major) and 6.46 (s, 1H minor), 5.95 (ddd, 1H major) and 5.59 (ddd, 1H minor), 5.20 (d, 1H major) and 5.02 (d, 1H minor), 5.18-5.15 (m, 1H), 5.11 (dd, 1H major) and 4.92 (dd, 1H minor), 3.65 (s, 3H major) and 3.62 (s, 3H minor), 3.26-3.11 (m, 1H), 1.18 (d, 3H minor) and 0.87 (d, 3H major).

Example 3A

2-[4-(5-Chloro-2-cyanophenyl)-5-methoxy-2-oxopyridin-1(2H)-yl]-3-methyl-N-(prop-2-en-1-yl)-pent-4-enamide (Racemic Mixture of Diastereomers)

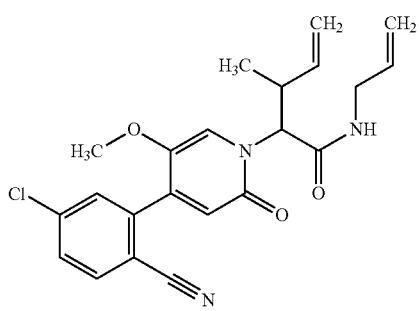 [SMILES: C=CCNC(=O)C(C(C)C=C)n1cc(OC)c(-c2cc(Cl)ccc2C#N)cc1=O]

2-[4-(5-Chloro-2-cyanophenyl)-5-methoxy-2-oxopyridin-1(2H)-yl]-3-methylpent-4-enoic acid (racemic mixture of diastereomers) (4.00 g, 10.7 mmol) and prop-2-en-1-amine (12 ml, 160 mmol) were dissolved in pyridine (40 ml) and heated to 60° C. A solution of T3P in ethyl acetate (19 ml, 50% purity, 32 mmol) was added dropwise and the mixture was further stirred at 60° C. for 1 h. Water was added and it was extracted three times with ethyl acetate. The combined organic layers were dried over sodium sulfate and the solvent was removed in vacuo. The residue was purified by column chromatography (silica gel; eluent: cyclohexane-ethyl acetate gradient) to yield 2.56 g (58% yield) of the title compound as racemic mixture of diastereomers.

LC-MS (Method 1): $R_t$=1.81 min; MS (ESIpos): m/z=412 $[M+H]^+$ $^1$H-NMR (400 MHz, DMSO-$d_6$): δ [ppm]=8.84 (t, 1H minor isomer) and 8.69 (t, 1H major isomer), 7.99 (d, 1H major) and 7.97 (d, 1H minor), 7.76-7.68 (m, 2H), 7.64 (s, 1H major) and 7.62 (s, 1H minor), 6.52 (s, 1H major) and 6.46 (s, 1H minor), 5.89-5.43 (m, 3H), 5.22-4.89 (m, 4H), 3.85-3.60 (m, 2H), 3.65 (s, 3H major) and 3.64 (s, 3H minor), 3.13-2.95 (m, 1H), 1.08 (d, 3H minor) and 0.83 (d, 3H major).

Example 4A tert-Butyl allyl{2-[4-(5-chloro-2-cyanophenyl)-5-methoxy-2-oxopyridin-1(2H)-yl]-3-methylpent-4-enoyl}carbamate (Racemic Mixture of Diastereomers)

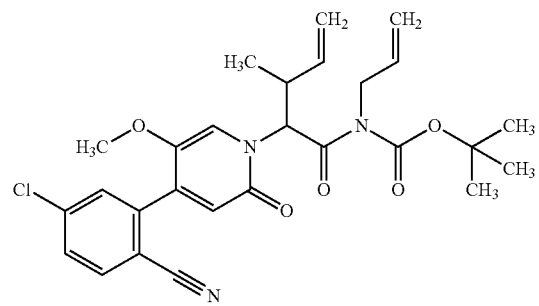 [SMILES: C=CCN(C(=O)OC(C)(C)C)C(=O)C(C(C)C=C)n1cc(OC)c(-c2cc(Cl)ccc2C#N)cc1=O]

2-[4-(5-Chloro-2-cyanophenyl)-5-methoxy-2-oxopyridin-1(2H)-yl]-3-methyl-N-(prop-2-en-1-yl)pent-4-enamide (racemic mixture of diastereomers) (2.50 g, 6.07 mmol) was dissolved in acetonitrile (120 ml). Di-tert-butyl dicarbonate (2.8 ml, 12 mmol) and 4-dimethylaminopyridine (297 mg, 2.43 mmol) were added and the mixture was heated to 60° C. for 1 h. The mixture was then concentrated in vacuo and the residue was directly purified by column chromatography (silica gel; eluent: cyclohexane-ethyl acetate gradient) to yield 3.07 g (99% yield) of the title compound as racemic mixture of diastereomers.

LC-MS (Method 1): $R_t$=2.41 min; MS (ESIpos): m/z=512 $[M+H]^+$ $^1$H-NMR (400 MHz, DMSO-$d_6$): δ [ppm]=7.99 (d, 1H major isomer) and 7.97 (d, 1H minor isomer), 7.75-7.63 (m, 2H), 7.42 (s, 1H major) and 7.39 (s, 1H minor), 6.51 (s, 1H major) and 6.46 (s, 1H minor), 6.45 (br. d, 1H major) and 6.36 (br. d, 1H minor), 5.96-5.58 (m, 2H), 5.22-4.92 (m, 4H), 4.24-4.07 (m, 2H), 3.66 (s, 3H major) and 3.62 (s, 3H minor), 3.35-3.20 (m, 1H), 1.484 (s, 9H minor) and 1.478 (s, 9H major), 1.16 (d, 3H minor) and 0.89 (d, 3H major).

Example 5A tert-Butyl 3-[4-(5-chloro-2-cyanophenyl)-5-methoxy-2-oxopyridin-1(2H)-yl]-4-methyl-2-oxo-2,3,4,7-tetrahydro-1H-azepine-1-carboxylate (Racemic Mixture of Diastereomers)

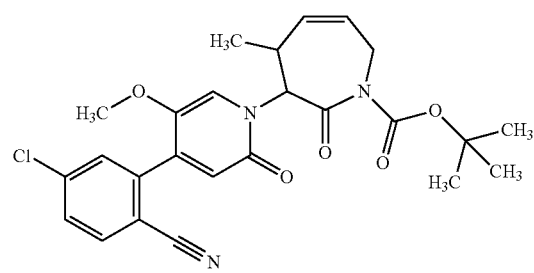 [SMILES: COc1cn(C2C(=O)N(C(=O)OC(C)(C)C)CC=CC2C)c(=O)cc1-c1cc(Cl)ccc1C#N]

17 tert-Butyl allyl{2-[4-(5-chloro-2-cyanophenyl)-5-methoxy-2-oxopyridin-1(2H)-yl]-3-methylpent-4-enoyl}carbamate (racemic mixture of diastereomers) (3.00 g, 5.86 mmol) was dissolved in dichloromethane (1.0 l) and the solution was degassed (argon atmosphere). Benzylidene [1,3-bis(2,4,6-trimethylphenyl)imidazolidin-2-ylidene]dichloridoruthenium-tricyclohexylphosphane (1/1) [CAS-RN 246047-72-3] (249 mg, 293 µmol) was added and the reaction was stirred at 45° C. for 1.5 h. Subsequently, saturated aq. sodium bicarbonate solution was added. The organic layer was separated and the aqueous layer was extracted twice with dichloromethane. The combined organic layers were washed with brine and dried over sodium sulfate. The solvent was evaporated and the residue was purified by column chromatography (silica gel; eluent: cyclohexane-ethyl acetate gradient) to yield 2.75 g (97% yield) of the title compound as racemic mixture of diastereomers.

LC-MS (Method 1): $R_t$=2.04 (major isomer) and 2.06 min (minor isomer); MS (ESIneg): m/z=482 [M−H]⁻

¹H-NMR (400 MHz, DMSO-d₆): δ [ppm]=8.01 (m, 1H minor isomer) and 8.00 (d, 1H major isomer), 7.78-7.71 (m, 2H), 7.47 (s, 1H major) and 7.31 (s, 1H, minor), 6.60 (s, 1H minor) and 6.56 (s, 1H major), 6.34 (d, 1H major) and 6.18 (d, 1H minor), 6.03-5.94 (m, 1H), 5.90-5.83 (m, 1H minor) and 5.83-5.77 (m, 1H major), 4.57 (dd, 1H minor) and 4.47 (dd, 1H major), 4.44-4.33 (m, 1H), 3.684 (s, 3H minor) and 3.676 (s, 3H major), 3.48-3.38 (m, 1H major), 3.07-2.97 (m, 1H minor), 1.46 (s, 9H major) and 1.45 (s, 9H minor), 1.18 (d, 3H minor) and 0.91 (d, 3H major).

Example 6A tert-Butyl 3-[4-(5-chloro-2-cyanophenyl)-5-methoxy-2-oxopyridin-1(2H)-yl]-4-methyl-2-oxoazepane-1-carboxylate (Racemic Mixture of Diastereomers)

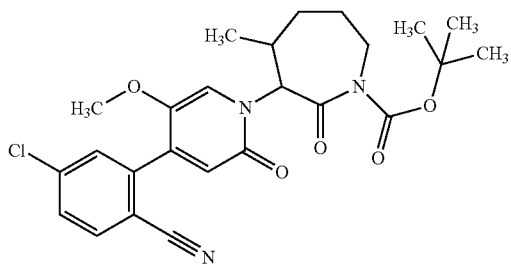 [SMILES: COc1cn(C2C(=O)N(C(=O)OC(C)(C)C)CCCC2C)c(=O)cc1-c1cc(Cl)ccc1C#N]

tert-Butyl 3-[4-(5-chloro-2-cyanophenyl)-5-methoxy-2-oxopyridin-1(2H)-yl]-4-methyl-2-oxo-2,3,4,7-tetrahydro-1H-azepine-1-carboxylate (racemic mixture of diastereomers) (2.70 g, 5.58 mmol) was dissolved in ethyl acetate (250 ml) and palladium (10% on charcoal, 594 mg) was added. The reaction was stirred under hydrogen (atmospheric pressure) for 4 h. The mixture was filtered through diatomaceous earth and the solvent was removed in vacuo. The residue was purified by column chromatography (silica gel; eluent: cyclohexane-ethyl acetate gradient) to yield 0.54 g of the major isomer of the starting material and 1.78 g (66% yield, 82% yield brsm) of the title compound as racemic mixture of diastereomers.

LC-MS (Method 1): $R_t$=2.05 min; MS (ESIneg): m/z=484 [M−H]⁻

18

¹H-NMR (400 MHz, DMSO-d₆): δ [ppm]=8.00 (d, 1H) and 7.99 (d, 1H), 7.77-7.71 (m, 2H), 7.42 (s, 1H minor isomer) and 7.16 (s, 1H major isomer), 6.56 (s, 1H major) and 6.52 (s, 1H minor), 5.89 (s, 1H major) and 5.86-5.66 (m, 1H minor), 4.23-4.13 (m, 1H), 3.68 (s, 3H major) and 3.66 (s, 3H minor), 3.65-3.55 (m, 1H), 2.64-2.56 (m, 1H) and (2.15-2.03 (m, 1H), 1.97-1.55 (m, 4H), 1.46 (s, 9H), 1.14 (d, 3H major) and 0.86 (d, 3H minor).

Example 7A

6-[(tert-Butoxycarbonyl)amino]-2-[4-(5-chloro-2-cyanophenyl)-5-methoxy-2-oxopyridin-1(2H)-yl]-3-methylhexanoic acid (Racemic Mixture of Diastereomers)

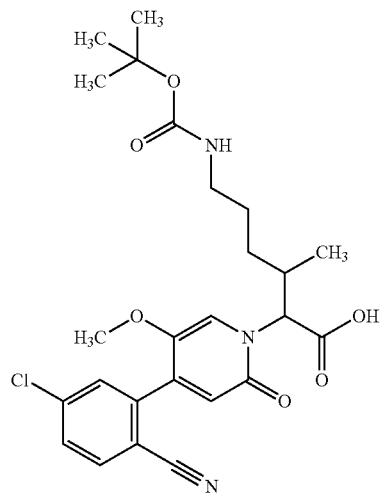 [SMILES: COc1cn(C(C(=O)O)C(C)CCCNC(=O)OC(C)(C)C)c(=O)cc1-c1cc(Cl)ccc1C#N]

tert-Butyl 3-[4-(5-chloro-2-cyanophenyl)-5-methoxy-2-oxopyridin-1(2H)-yl]-4-methyl-2-oxoazepane-1-carboxylate (racemic mixture of diastereomers) (1.77 g, 3.64 mmol) was dissolved in THF (25 ml) and an aq. solution of lithium hydroxide (3.6 ml, 2.0 M, 7.2 mmol) was added. The mixture was stirred at 30° C. for 1 h, then concentrated in vacuo and the residue was dissolved in water. It was washed with ethyl acetate. The aqueous phase was acidified with 1N aq. hydrochloric acid and extracted twice with ethyl acetate. The combined organic layers were washed with brine and dried over sodium sulfate to yield 1.78 g (97% yield) of the title compound as racemic mixture of diastereomers.

LC-MS (Method 1): $R_t$=1.80 min (minor isomer) and 1.84 min (major isomer); MS (ESIpos): m/z=504 [M+H]⁺

¹H-NMR (400 MHz, DMSO-d₆): δ [ppm]=13.13 (br. s, 1H), 8.01-7.97 (m, 1H), 7.76-7.71 (m, 2H), 7.38 (s, 1H), 6.80 (br. t, 1H major isomer) and 6.70 (br. t, 1H minor isomer), 6.51 (s, 1H), 5.10 (d, 1H minor) and 5.05 (d, 1H major), 3.64 (s, 3H minor) and 3.63 (s, 3H major), 3.01-2.71 and 2.49-2.37 (m, together 3H), 1.64-1.40 and 1.31-1.13 and 1.02-0.93 (m, together 4H), 1.38 (s, 9H major) and 1.34 (s, 9H minor), 1.05 (d, 3H minor) and 0.72 (d, 3H major).

Example 8A tert-Butyl {6-[(3-carbamoylpyrazolo[1,5-a]pyridin-5-yl)amino]-5-[4-(5-chloro-2-cyanophenyl)-5-methoxy-2-oxopyridin-1(2H)-yl]-4-methyl-6-oxohexyl}carbamate (Racemic Mixture of Diastereomers)

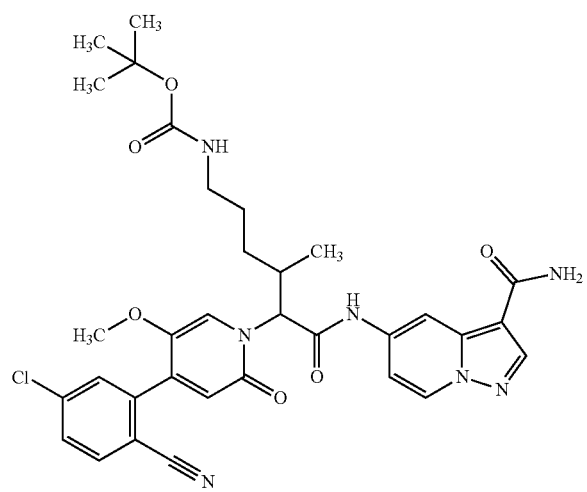 [SMILES: COc1cn(C(C(=O)Nc2ccn3ncc(C(N)=O)c3c2)C(C)CCCNC(=O)OC(C)(C)C)c(=O)cc1-c1cc(Cl)ccc1C#N]

6-[(tert-Butoxycarbonyl)amino]-2-[4-(5-chloro-2-cyanophenyl)-5-methoxy-2-oxopyridin-1(2H)-yl]-3-methylhexanoic acid (racemic mixture of diastereomers) (1.08 g, 2.14 mmol) and 5-aminopyrazolo[1,5-a]pyridine-3-carboxamide trifluoroacetate [CAS-RN 1891071-11-6; WO2016/046158, p. 53, expl. 1.1 C] (746 mg, 2.57 mmol) were dissolved in DMF (4.0 ml). HATU (1.22 g, 3.21 mmol) as solution in DMF (2.0 ml) and subsequently N,N-diisopropylethylamine (370 μl, 2.1 mmol) were added dropwise. The reaction was stirred for 1.5 h at room temperature. Further 5-aminopyrazolo[1,5-a]pyridine-3-carboxamide trifluoroacetate (187 mg, 643 μmol) and N,N-diisopropylethylamine (370 μl, 2.1 mmol) were added. After stirring overnight, additional HATU (407 mg, 1.07 mmol) and N,N-diisopropylethylamine (370 μl, 2.1 mmol) were added and after 1 h the reaction was concentrated in vacuo. The residue was crystallized with water, collected by suction filtration and washed with water and dried in vacuo. The compound was purified by column chromatography (silica gel; eluent: dichloromethane/methanol gradient) to yield 1.20 g (84% yield) of the title compound as racemic mixture of diastereomers.

LC-MS (Method 1): $R_t$=1.75 min; MS (ESIpos): m/z=662 [M+H]$^+$ $^1$H-NMR (400 MHz, DMSO-d$_6$): δ [ppm]=11.14 (br. s, 1H major isomer) and 11.12 (br. s, 1H minor isomer), 8.73-8.66 (m, 2H), 8.47 (s, 1H major) and 8.46 (s, 1H minor), 8.00 (d, 1H major) and 7.99 (d, 1H minor), 7.77-7.71 (m, 2H), 7.63 (s, 1H), 7.60 (br. s, 1H), 7.26 (dd, 1H), 6.98 (br. s, 1H), 6.76-6.70 (m, 1H), 6.56 (s, 1H minor) and 6.55 (s, 1H major), 5.57 (d, 1H major) and 5.56 (d, 1H minor), 3.72 (s, 3H major) and 3.71 (s, 3H minor), 2.96-2.76 (m, 2H), 1.64-0.96 (m, 5H), 1.34 (s, 9H major) and 1.28 (s, 9H minor), 1.05 (d, 3H major) and 0.78 (d, 3H minor).

The separation of the four stereoisomers can be achieved by chiral chromatography: Column and solid phase: 250 mm×20 mm, Chiralpak IE, 5 μm; Eluent: Ethanol; Flow 15.0 ml/min. Yields three peaks (7.0-8.5 min, 11.1 min, 13.9 min). The first peak needs further chromatography for separation: Column and solid phase: 250 mm×20 mm, Chiralpak IC, 5 μm; Eluent: Ethanol; Flow 15.0 ml/min. Yields two peaks (6.29 min, 7.33 min).

Analytical HPLC: Column 250 mm×4.6 mm, Chiralcel OX-H, 5 μm; Eluent: iso-hexane/ethanol 1:1; Flow 1.0 ml/min; Temperature: 40° C.

Stereoisomer 1: $R_t$=10.90 min.
Stereoisomer 2: $R_t$=7.50 min.
Stereoisomer 3: $R_t$=8.85 min.
Stereoisomer 4: $R_t$=9.19 min.

Stereoisomer 1 and 4 as well as stereoisomer 2 and 3 are enantiomeric to each other.

Stereoisomer 1 and 4:

$^1$H-NMR (400 MHz, DMSO-d$_6$): δ [ppm]=11.14 (br. s, 1H), 8.70-8.67 (m, 2H), 8.47 (s, 1H), 8.00 (d, 1H), 7.75-7.71 (m, 2H), 7.60 (br. s, 1H), 7.62 (br. s, 1H), 7.25 (dd, 1H), 6.98 (br. s, 1H), 6.76-7.70 (m, 1H), 6.55 (s, 1H), 5.57 (d, 1H), 3.71 (s, 3H), 2.93-2.74 (m, 2H), 1.52-1.29 (m, 3H), 1.34 (s, 9H), 1.26-0.96 (m, 2H), 1.05 (d, 3H).

Stereoisomer 2 and 3:

$^1$H-NMR (400 MHz, DMSO-d$_6$): δ [ppm]=11.12 (br. s, 1H), 8.71 (d, 1H), 8.68 (d, 1H), 8.46 (s, 1H), 7.99 (d, 1H), 7.76 (d, 1H), 7.73 (dd, 1H), 7.62 (s, 1H), 7.59 (br. s, 1H), 7.25 (dd, 1H), 6.99 (br. s, 1H), 6.75 (br. t, 1H), 6.56 (s, 1H), 5.56 (d, 1H), 3.70 (s, 3H), 2.95-2.83 (m, 2H), 2.48-2.39 (m, 1H), 1.66-1.53 (m 1H), 1.51-1.29 (m 3H), 1.28 (s, 9H), 0.77 (d, 3H).

WORKING EXAMPLES

Example 1

5-({6-Amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamidetrifluoroacetate (Racemic Mixture of Diastereomers)

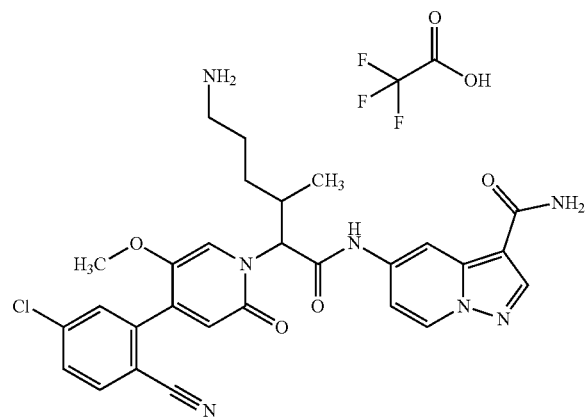 [SMILES: COc1cn(C(C(=O)Nc2ccn3ncc(C(N)=O)c3c2)C(C)CCCN)c(=O)cc1-c1cc(Cl)ccc1C#N ; O=C(O)C(F)(F)F]

tert-Butyl {6-[(3-carbamoylpyrazolo[1,5-a]pyridin-5-yl)amino]-5-[4-(5-chloro-2-cyanophenyl)-5-methoxy-2-oxopyridin-1(2H)-yl]-4-methyl-6-oxohexyl}carbamate (racemic mixture of diastereomers) (1.20 g, 1.81 mmol) was dissolved in dichloromethane and cooled with water ice. Trifluoroacetic acid (2.8 ml, 36 mmol) was added. The mixture was warmed to room temperature and stirred for 1 h. The mixture was then evaporated. Dichloromethane was added and removed in vacuo. This procedure was once repeated. The residue was purified by column chromatography (silica gel; eluent: dichloromethane/methanol gradient) to yield 785 mg (64% yield) of the title compound as racemic mixture of diastereomers.

LC-MS (Method 2): $R_t$=0.64 min (major isomer) 0.68 (minor isomer); MS (ESIpos): m/z=562 [M+H]$^+$ $^1$H-NMR (400 MHz, DMSO-$d_6$): δ [ppm]=11.17 (s, 1H major isomer) and 11.14 (s, 1H minor isomer), 8.73-8.67 (m, 2H), 8.48 (s, 1H), 8.00 (d, 1H major) and 7.99 (d, 1H minor), 7.76-7.72 (m, 2H), 7.69 (br. s, 4H), 7.65 (s, 1H major) and 7.61 (s, 1H minor), 7.28-7.25 (m, 1H), 6.98 (br. s, 1H), 6.58 (s, 1H minor) and 6.57 (s, 1H major), 5.61-5.55 (m, 1H), 3.72 (s, 3H major) and 3.70 (s, 3H minor), 2.87-2.51 (m, 3H), 1.80-1.09 (m, 4H), 1.08 (d, 3H major) and 0.79 (d, 3H minor).

Example 2

5-({(2S)-6-Amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide trifluoroacetate (Stereoisomer 3)

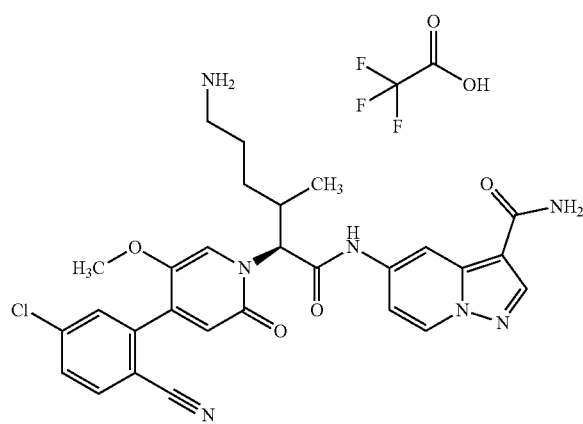 [SMILES: COc1cn([C@H](C(=O)Nc2ccn3ncc(C(N)=O)c3c2)C(C)CCCN)c(=O)cc1-c1cc(Cl)ccc1C#N ; O=C(O)C(F)(F)F]

Following the procedure mentioned in Example 1 the separated carbamate of Example 8A stereoisomer 3 was deprotected individually.

Stereoisomer 3:

LC-MS (Method 1): $R_t$=1.05 min; MS (ESIpos): m/z=562 [M+H]$^+$ $^1$H-NMR (400 MHz, DMSO-$d_6$): δ [ppm]=11.15 (s, 1H), 8.72 (d, 1H), 8.69 (d, 1H), 8.48 (s, 1H), 8.00 (d, 1H), 7.76-7.72 (m, 2H), 7.60 (s, 1H), 7.63 (br s, 4H), 7.27 (dd, 1H), 6.98 (br s, 1H), 6.58 (s, 1H), 5.56 (d, 1H), 3.70 (s, 3H), 2.88-2.72 (m, 2H), (1H under DMSO), 1.81-1.67 (m, 1H), 1.63-1.44 (m, 2H), 1.39-1.28 (m, 1H), 0.79 (d, 3H).

Example 3

5-({(2S)-6-Amino-2-[4-(5-chloro-2-cyanophenyl)-5-methoxy-2-oxopyridin-1(2H)-yl]-3-methylhexanoyl}amino)pyrazolo[1,5-a]pyridine-3-carboxamide trifluoroacetate (stereoisomer 4)

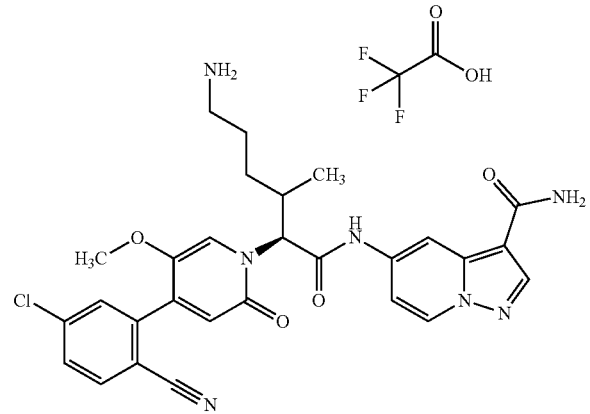 [SMILES: COc1cn([C@H](C(=O)Nc2ccn3ncc(C(N)=O)c3c2)C(C)CCCN)c(=O)cc1-c1cc(Cl)ccc1C#N ; O=C(O)C(F)(F)F]

Following the procedure mentioned in Example 1 the separated carbamate of Example 8A stereoisomer 4 was deprotected individually.

Stereoisomer 4:

LC-MS (Method 1): $R_t$=0.99 min; MS (ESIpos): m/z=562 [M+H]$^+$ $^1$H-NMR (400 MHz, DMSO-$d_6$): δ [ppm]=11.17 (s, 1H), 8.72-8.67 (m, 2H), 8.48 (s, 1H), 8.03-7.98 (m, 1H), 7.77-7.72 (m, 2H), 7.65 (s, 1H), 7.62 (br s, 4H), 7.26 (dd, 1H), 6.98 (br s, 1H), 6.57 (s, 1H), 5.59 (d, 1H), 3.72 (s, 3H), 2.83-2.62 (m, 2H), 2.58-2.51 (m, 1H), 1.70-1.44 (m, 2H), 1.08 (d, 3H), 1.26-1.06 (m, 2H).

B) ASSESSMENT OF PHYSIOLOGICAL EFFICACY

The suitability of the compounds according to the invention for treating thromboembolic disorders can be demonstrated in the following assay systems:

a) Test Descriptions (In Vitro)

a.1) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 μM to 0.0078 μM; resulting final concentrations in the test: 50 μM to 0.00013 μM). In each case 1 μl of the diluted substance solutions is placed into the wells of white microtitre plates from Greiner (384 wells). 20 μl of assay buffer (50 mM Tris/HCl pH 7.4; 100 mM sodium chloride solution; 5 mM of calcium chloride solution; 0.1% of bovine serum albumin) and 20 μl of plasma kallikrein from Kordia (0.6 nM in assay buffer) are then added successively. After 15 min of incubation, the enzyme reaction is started by addition of 20

µl of the substrate H-Pro-Phe-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table A below (some as mean values from multiple independent individual determinations):

TABLE A

| Example No. | $IC_{50}$ [nM] |
| --- | --- |
| 1 | 5.6 |
| 2 | 1.8 |
| 3 | 2.1 | a.2) Measurement of FXIa Inhibition

The factor XIa inhibition of the substances according to the invention is determined using a biochemical test system which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions is placed into the wells of white microtitre plates from Greiner (384 wells). 20 µl of assay buffer (50 mM of Tris/HCl pH 7.4; 100 mM of sodium chloride; 5 mM of calcium chloride; 0.1% of bovine serum albumin) and 20 µl of factor XIa from Kordia (0.45 nM in assay buffer) are then added successively. After 15 min of incubation, the enzyme reaction is started by addition of 20 µl of the factor XIa substrate Boc-Glu(OBzl)-Ala-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table B below (some as mean values from multiple independent individual determinations):

TABLE B

| Example No. | $IC_{50}$ [nM] |
| --- | --- |
| 1 | >10000 |
| 2 | >2000 |
| 3 | >2000 | a.3) Determination of the Selectivity

To demonstrate the selectivity of the substances with respect to FXIa inhibition, the test substances are examined for their inhibition of other human serine proteases, such as factor Xa, trypsin and plasmin. To determine the enzymatic activity of factor Xa (1.3 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of NaCl, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 µmol/l of Boc-Ile-Glu-Gly-Arg-AMC from Bachem for factor Xa and trypsin, 50 µmol/l of MeOSuc-Ala-Phe-Lys-AMC from Bachem for plasmin). After an incubation time of 30 min at 22° C., fluorescence is measured (excitation: 360 nm, emission: 460 nm). The measured emissions of the test mixtures with test substance are compared to the control mixtures without test substance (only dimethyl sulphoxide instead of test substance in dimethyl sulphoxide) and $IC_{50}$ values are calculated from the concentration/activity relationships.

a.4) Determination of Anticoagulatory Activity

The anticoagulatory activity of the test substances is determined in vitro in human plasma and rat plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 4000 g for 15 minutes. The supernatant is pipetted off.

The activated partial thromboplastin time (APTT) is determined in the presence of varying concentrations of test substance or the corresponding solvent using a commercial test kit (aPTT reagent from Siemens). The test compounds are incubated with the plasma and the aPTT reagent at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of Endothelium Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, NY), it is possible to measure continuously variations in the transendothelial electrical resistance (TEER) across an endothelial cell monolayer plated over gold electrodes. HUVECs are sown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1\times10^{-10}$ to $1\times10^{-6}$ M.

a.6) Determination of the In Vitro Permeability of Endothelial Cells

In a further hyperpermeability model, the activity of the substances on the modulation of macromolecular permeability is determined. HUVECs are sown on a fibronectin-coated Transwell filter membrane (24-well plates, 6.5 mm insert with 0.4 µM polycarbonate membrane; Costar #3413). The filter membrane separates the upper from the lower cell culture space, with the confluent endothelial cell layer on the floor of the upper cell culture space. 250 g/ml of 40 kDa FITC dextan (Invitrogen, D1844) are added to the medium of the upper chamber. Hyperpermeability of the monolayer is induced by stimulation with kininogen, prekallikrein and factor XII (100 nM each). Every 30 min, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1 \times 10^{-10}$ to $1 \times 10^{-6}$ M.

b) Determination of Antithrombotic Activity (In Vivo)

b.1) Arterial Thrombosis Model (Iron(II) Chloride-Induced Thrombosis) in Combination with Ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined.

Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the vessel injury is then caused by wrapping a piece of filter paper (10 mm×10 mm) on a Parafilm® strip (25 mm×12 mm) around the carotid artery without disturbing the blood flow. The filter paper contains 100 µL of a 13% strength solution of iron(II) chloride (Sigma) in water. After 5 min, the filter paper is removed and the vessel is rinsed twice with aqueous 0.9% strength sodium chloride solution. 30 min after the injury the injured region of the carotid artery is extracted surgically and any thrombotic material is removed and weighed.

The test substances are administered either intravenously to the anaesthetized animals via the femoral vein or orally to the awake animals via gavage, in each case 5 min and 2 h, respectively, before the injury.

Ear bleeding time is determined 2 min after injury to the carotid artery. To this end, the left ear is shaved and a defined 3-mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Edema Formation and/or Neovascularization in the Eye (In Vivo)

c.1) Test of the Efficacy of Substances in the Laser-Induced Choroidal Neovascularization Model This study serves to investigate the efficacy of a test substance on reduction of extravasation/edema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine). Following instillation of a drop of a 0.5% strength tropicamide solution to dilate the pupils, choroidal neovascularization is triggered on six defined locations around the optical nerve using a 532 nm argon laser photocoagulator (diameter 50-75 µm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 min later, pictures of the eye background are taken. The degree of extravasation/the edema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and µm, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57Bl/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% Formalin. After washing in phosphate-buffered saline, the retina is excised, a flat preparation thereof is produced and this is stained with isolectin B4 antibody. Quantification of neovascularization is carried out using a Zeiss ApoTome.

C) WORKING EXAMPLES OF PHARMACEUTICAL COMPOSITIONS

The substances according to the invention can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).

Oral Suspension:

Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:

The Rhodigel is suspended in ethanol, and the compound of Example 1 is added to the suspension. The water is added while stirring. The mixture is stirred for about 6 h until swelling of the Rhodigel is complete.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

The invention claimed is:

1. Compound 5-({6-amino-2-[4-(5-chloro-2-cyanophenyl)-5-methoxy-2-oxopyridin-1 (2H)-yl]-3-methylhexanoyl} amino)pyrazolo[1,5-a]pyridine-3-carboxamide of formula (I)

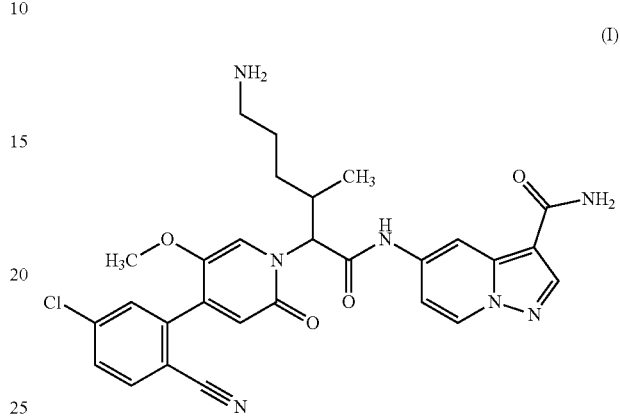

(I)

or one of the salts thereof, solvates thereof or solvates of the salts thereof.

2. The compound of claim 1, wherein the compound is the salt 5-({6-amino-2-[4-(5-chloro-2-cyanophenyl)-5-methoxy-2-oxopyridin-1 (2H)-yl]-3-methylhexanoyl} amino)pyrazolo[1,5-a]pyridine-3-carboxamide trifluoroacetate of formula (Ia)

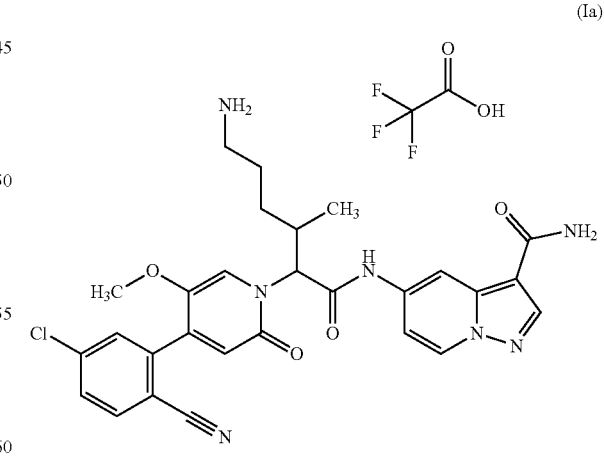

(Ia)

or one of the solvates thereof.

3. The compound 5-({6-amino-2-[4-(5-chloro-2-cyanophenyl)-5-methoxy-2-oxopyridin-1 (2H)-yl]-3-methylhexanoyl} amino)pyrazolo[1,5-a]pyridine-3-carboxamide according to claim 1 of the formula (Ib)

(Ib)

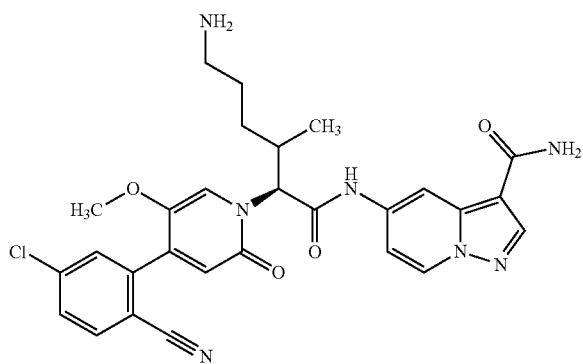

or one of the salts, solvates or solvates of the salts thereof.

4. A medicament comprising a compound according to claim 1 and one or more pharmaceutically suitable excipients.

5. A method for the treatment of thrombotic or thromboembolic disorders, comprising administering a therapeutically effective amount of a compound according to claim 1 to a patient in need.

6. A method for preventing coagulation ex vivo, for the protection of organs to be transplanted and for preserving blood and plasma products, comprising applying to the organs, blood or products an effective amount of a compound of claim 1.

7. A method for preventing the coagulation of blood in vitro, in banked blood or biological samples, comprising adding an anticoagulatory effective amount of the compound according to claim 1 to the banked blood or biological samples.

* * * * *